United States Patent [19]

Weitz et al.

[11] 4,239,911

[45] Dec. 16, 1980

[54] MANUFACTURE OF GLYCOL ESTERS

[75] Inventors: Hans-Martin Weitz, Bad Duerkheim; Juergen Hartig, Ludwigshafen, both of Fed. Rep. of Germany

[73] Assignee: BASF Aktiengesellschaft, Fed. Rep. of Germany

[21] Appl. No.: 800,022

[22] Filed: May 24, 1977

[30] Foreign Application Priority Data

May 26, 1976 [DE] Fed. Rep. of Germany ....... 2623562

[51] Int. Cl.$^3$ ..................... C07C 67/05; C07C 69/08; C07C 69/16
[52] U.S. Cl. .................................. 560/246; 560/234; 568/858
[58] Field of Search ............... 560/246, 112, 243, 244; 260/410.6

[56] References Cited

U.S. PATENT DOCUMENTS

| | | | |
|---|---|---|---|
| 2,497,408 | 2/1950 | Gresham | 560/246 |
| 3,755,423 | 8/1973 | Onoda et al. | 560/244 |
| 3,965,152 | 6/1976 | Smith et al. | 560/243 |
| 3,965,156 | 6/1976 | Smith et al. | 560/243 |

*Primary Examiner*—Vivian Garner
*Attorney, Agent, or Firm*—Keil & Witherspoon

[57] ABSTRACT

Alkylene glycol dicarboxylates are obtained by reacting carboxylic acid esters of monohydric or polyhydric aliphatic short-chain alcohols with an olefin and oxygen in the presence of a catalyst, a hydrolyzing agent and water.

6 Claims, 1 Drawing Figure

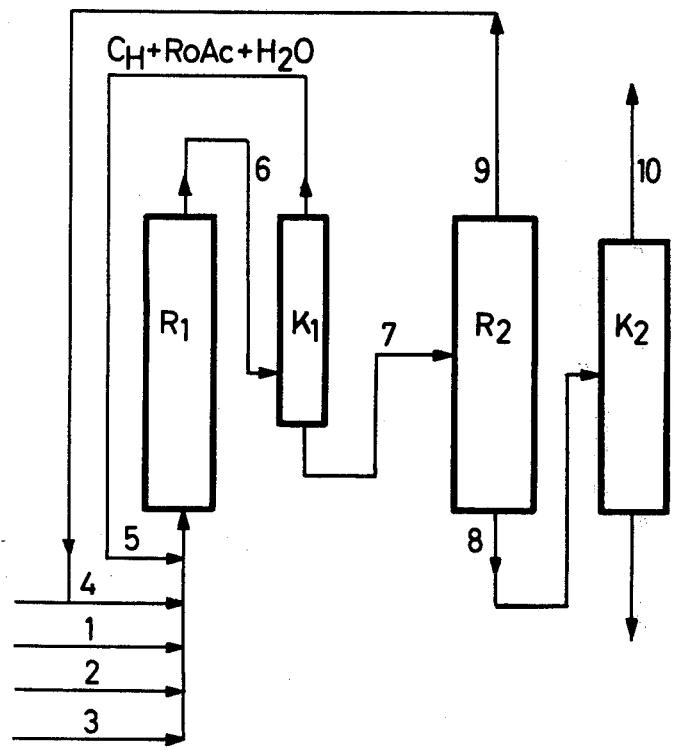

MANUFACTURE OF GLYCOL ESTERS

The present invention relates to a process for the manufacture of ethylene glycol diformate and diacetate or 1,2-propylene glycol diformate and diacetate by reacting ethylene or propylene and molecular oxygen with formic acid or acetic acid, in the presence of an oxyacylation catalyst. This process is conventionally referred to as oxyacylation and acetoxylation, respectively.

The invention further relates to a process for the manufacture of ethylene glycol and 1,2-propylene glycol.

The process to which the present invention relates is disclosed, inter alia, in German Laid-Open Applications DOS No. 1,948,787 and 1,948,856 as well as in German Laid-Open Applications DOS No. 2,120,003, 2,120,004, 2,120,005 and 2,303,867. The process improvements hitherto disclosed essentially concerned suitable catalysts and advantageous arrangements for carrying out the process.

Glycol esters are intermediates in, for example, the manufacture of vinyl acetate and of glycols. If glycols are produced from glycol esters, the acid is usually recycled, various working-up stages being interpolated.

A problem in recycling the acid is the fact that equilibrium considerations require the use of a large excess of water when carrying out the (acid) hydrolysis of the ester, and a reaction mixture of glycol and water and, for example, acetic acid, which is difficult to separate, is obtained. It is known that the non-ideal boiling characteristics of water/acetic acid mixtures are responsible for the high energy consumption entailed in the separation. The recycling of the acetic acid resulting from the hydrolysis of the glycol diacetate furthermore presents corrosion problems.

It is an object of the present invention to avoid the above disadvantages.

We have found that this object is achieved and that ethylene glycol diformate or diacetate or 1,2-propylene glycol diformate or diacetate is obtained in an advantageous manner by reacting ethylene or propylene and molecular oxygen in the presence of an oxyacylation catalyst, if an ester of formic acid or acetic acid with a short-chain monohydric or polyhydric alcohol, i.e., an alcohol of 1 to 5 carbon atoms, preferably methyl acetate or ethyl acetate, is used as the agent supplying carboxylic acid. The glycol ester obtained in the reaction may be used itself in place of the free carboxylic acid. The reaction is carried out in the presence of a hydrolysis catalyst and of not less than 1 mole of water per mole of olefin to be converted.

Optionally, the hydrolysis may be carried out in a separate preliminary reaction stage; in that case, instead of the ester, a mixture, e.g., the mixture corresponding to the acid hydrolysis equilibrium, of the ester with the carboxylic acid, the alcohol and water is fed to the actual reaction (i.e., the oxyacylation). Preferably, however, the hydrolysis is carried out in the course of the actual oxyacylation, i.e., in the same reaction vessel.

The advantage of the process according to the invention is essentially that the carboxylic acid esters are more easily handled than the carboxylic acids.

Surprisingly, the oxyacylation reaction is insensitive to the presence of even substantial amounts of water; for economic reasons, however, the presence of unnecessarily large amounts of water is undesirable. Preferably, therefore, the reaction is carried out in the presence of an amount of water corresponding to that given by the equation

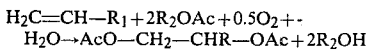
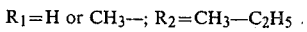

$R_1 = H$ or $CH_3$—; $R_2 = CH_3$—$C_2H_5$.

(i.e., 1 mole of water per mole of ethylene or propylene), or which does not exceed this by a substantial amount, e.g., by up to 10 moles. Only practical considerations impose a limit on the use of larger amounts of water.

In view of the fact that the most important desired product of the reaction of ethylene or propylene with carboxylic acid and oxygen is the corresponding 1,2-glycol, the invention further relates to the manufacture of ethylene glycol and/or 1,2-propylene glycol by reacting ethylene or propylene with molecular oxygen and a carboxylic acid ester in the presence of a catalyst, and carrying out a hydrolysis, the recovered acid being recycled. In that case, the invention may result in a technique involving carrying out the hydrolysis of the glycol diester in the presence of a short-chain aliphatic alcohol and recycling the alkyl ester (which may or may not first be purified) obtained by trans-esterification; alternatively, the glycol ester itself may be recycled to the reaction, a glycol ester being formed which contains free glycol, the free glycol being removed. The aliphatic alcohol or the glycol can travel with the mixture through the entire reaction zone and does not interfere. For the prior art, reference may be made to German Laid-Open Applications DOS Nos. 2,425,761, 2,425,843 and 2,425,878. It is advantageous to carry out the trans-esterification in the presence of an excess of, for example, from 1 to 10 moles of the alcohol.

It is true that German Laid-Open Application DOS No. 2,503,748 discloses that the reaction of ethylene, oxygen and acetic acid, to give vinyl acetate, can also be carried out with methyl acetate and water if an acid co-catalyst is present. However, this process is not comparable with the process of the present invention, inter alia because in the earlier process a different and substantially more active catalyst is used; the addition of substantial amounts of water and the interpolation of a preliminary hydrolysis step result in a desirable reduction in the rate of reaction of the process for the manufacture of vinyl acetate. Inherently, however, the process for the manufacture of vinyl acetate does not consume a stoichiometric amount of water, so that this other process in principle is feasible with catalytic amounts of water.

Where the process according to the invention is concerned with the oxidative addition reaction between the carboxylic acid and ethylene or propylene (oxacylation), it is carried out in the presence of special catalysts. It should merely be mentioned briefly that the catalysts concerned contain transition metal compounds, eg. compounds of Te, Ce, Sb, Mn, V, Ga, As, Co and the like, in conjunction with a halogen or a hydrohalic acid. The use of different catalysts is also possible, as a rule.

The catalyst required for the hydrolysis of the alkyl ester may be a hydrohalic acid which is present in some of the processes mentioned above. It is also possible to use a certain amount of a pre-hydrolyzate of the ester containing a certain amount of the free acid itself, the hydrolyzate and the acid being soluble in the reaction mixture. It is also possible to use some other mineral acid as the catalyst.

The amount and concentration of the catalyst should be such that the rate of hydrolysis of the ester is greater than the rate of the oxyacylation reaction, so that the latter can proceed. In the case of methyl acetate, this is, for example, a concentration of from 80 to 300 milliequivalents of acid per mole of ester converted per hour, i.e., with the conventionally achievable rate of the main reaction, an acidity of from 0.1 N to 3 N will suffice. If the main reaction is carried out in the presence of, for example, hydrobromic acid, its concentration as a rule suffices to give the desired hydrolysis rate.

The reaction temperature is that conventionally used for oxyacylations and is, for example, from 100° to 200° C. Because of the low solubility of the olefin and the oxygen in the reaction mixture at atmospheric pressure, the reaction is as a rule carried out at pressures above atmospheric, preferably 10 to 200 bars. Instead of oxygen, oxygen-containing gas mixtures, e.g., air, can be used. The reaction can be carried out in the absence of a gas phase, e.g., exclusively with dissolved oxygen and olefin. Conversion rates of 600 g of glycol ester (mixture) per 1,000 g of catalyst metal per hour are achieved.

Since the reaction mixture carries with it substantial amounts of the alcohol used during the hydrolysis, the latter can be utilized to recover the alkyl acetate or alkyl formate obtained in the subsequent transesterification step. An advantageous procedure is to heat the reaction mixture containing the alcohol and water, and to distill off the relatively low-boiling alkyl ester. This leaves ethylene glycol or propylene glycol, which may still contain a certain amount of carboxylic acid and water, from which the pure products are isolated in the conventional manner. The lower alkyl formates and alkyl acetates form an azeotrope with water, containing from about 5 to 10% of the latter, which may be recycled. As has been pointed out, water is consumed during the oxyacylation and this will be made up at least partly by recycling. According to the invention, the use of methyl acetate and ethyl acetate is preferred. In principle, the process also succeeds with the corresponding formic acid esters; for example, methyl formate can be used.

The low molecular weight alcohol or its ester can be regarded as a vehicle for the carboxylic acid. As has been pointed out, the carboxylic acid bonded to the glycol itself can also be recycled to the oxyacylation reaction in the form of the glycol ester itself, since all that matters is the availability of the carboxylic acid during the reaction; in such a case, the glycol ester is recycled after isolating the glycol contained therein. To understand this situation, it is necessary to visualize that the glycol ester is hydrolyzed to give the acid and glycol, the acid being consumed for the formation of fresh glycol ester.

In the case of this procedure it is, however, to be borne in mind that side reactions, e.g., the etherification of the free diol with free alcohol or with itself, can cause some loss of the vehicle, which may have to be made up.

Two embodiments of the process can be used for the transesterification of the glycol ester with a low molecular weight alcohol (especially methanol).

It has already been mentioned briefly that the trans-esterification can be acid-catalyzed. In this case, the reaction mixture in general has to contain a certain amount of water, an acid hydrolysis catalyst, e.g., an acid ion exchanger, or an aqueous acid.

On the other hand, the trans-esterification can also be carried out with catalytic (i.e., non-stoichiometric) amounts of alkali, e.g., with sodium alcoholate or with a solution of a catalytic amount of an alkali metal hydroxide in the low molecular weight alcohol. In this case, the presence of substantial amounts of water may be less desirable; preferably this reaction is carried out in the absence of water.

In each case, the conventional rules for working with catalysts apply.

An apparatus which may be used with advantage for carrying out the reaction is shown in the figure.

In this apparatus, oxygen (1), water (2) and olefin (3) together with an alkyl ester (4) or a recycle stream of products (5) that have not been converted in the first pass are fed to a reaction chamber ($R_1$) which should contain an acid catalyst and an oxyacylation catalyst; in a downstream column ($K_1$), the reaction mixture (6) is separated into low-boiling unconverted compounds (olefins) (5) and the glycol ester as well as certain amounts of glycol half-ester and glycol or alcohol (7). The latter are separated in a distillation column ($R_2$) into glycol (8) and a mixture of low-boiling products (9) which contains alkyl ester and/or glycol ester and water and may or may not contain alcohol; a trans-esterification may take place during this separation. The equipment used to control this trans-esterification (alcohol circulation, acid metering, reflux condenser and the like) are not shown in the figure. The desired product, the glycol (8), is subjected to a refining purification ($K_3$;10).

EXAMPLE 1

300 g of methyl acetate (4.05 moles), 7 g of tellurium dioxide and 27.7 g of 47 percent strength hydrobromic acid are introduced into a tantalum-lined 1 liter autoclave. 21 liters (S.T.P.) of ethylene and 9 liters (S.T.P.) of oxygen are introduced into the autoclave at room temperature. The autoclave is then shaken for 5 hours at 160° C. After cooling and letting down, during which 34.8 liters (S.T.P.) of gases containing 1.5% by volume of oxygen, 1.1% by volume of carbon dioxide and less than 0.02% by volume of carbon monoxide are released (the remainder of the gas mixture consisting of ethylene and chemically inert gases), the liquid contents of the autoclave, amounting to 288.7 g, are filtered. The liquid contains 2.65% by weight of water. After distillation under reduced pressure, 8.9 g of a mixture of 55% of glycol diacetate, 26% of glycol monoacetate and 16% of glycol are obtained. The first runnings contain small amounts of methyl bromoacetate, bromoethyl acetate and bromoethanol, which can be recycled as catalyst or reaction intermediates. The conversion of ethylene is 6.5%, the oxygen conversion being almost complete. The ethylene conversion is calculated from the total moles of ethylene derivatives formed, relative to the ethylene initially introduced.

EXAMPLE 2

300 g of methyl acetate, 7 g of tellurium oxide, 27.7 g of hydrobromic acid and 90 ml of liquid propylene, as well as 12 liters (S.T.P.) of gaseous oxygen are introduced into the apparatus described in Example 1. The autoclave is shaken for 5 hours at 160° C. After completion of the reaction, the pressure is let down, 8.5 liters (S.T.P.) of gaseous products being released. These contain 5.45% by volume of oxygen, 0.02% by volume of carbon monoxide, 4.0% by volume of carbon dioxide and unconverted propylene and a small amount of inert gases. The liquid reaction mixture, which weighs 328 g and contains 3.26 percent by weight of water, is filtered, concentrated in a rotary evaporator and distilled under reduced pressure. 16.5 g of distillate having the following composition are obtained: 25.8% of propylene glycol diacetate, 39.0% of 1-acetoxypropan-2-ol, 18.8% of 2-acetoxypropan-1-ol and 15.4% of 1,2-propanediol (propylene glycol).

The conversion, based on propylene initially introduced, is 13 mole %. The space-time yield, based on 1 kg of catalyst, is 470 g per hour. The selectivity (calculated from the carbon balance determined by gas chromatography) is 86%.

We claim:

1. In a one-step liquid phase process for the manufacture of ethylene glycol diformate or diacetate or 1,2-propylene glycol diformate or diacetate by reacting ethylene or propylene, molecular oxygen and the appropriate carboxylic acid in a reaction chamber and in the presence of an effective amount of oxyacylation catalyst containing a compound of a transition metal selected from the group of Te, Ce, Sb, Mn, V, Ga, As and Co in conjuction with a halogen or a hydrohalic acid, the improvement which comprises:

using an ester of formic acid or acetic acid with a short-chain aliphatic alcohol of 1–5 carbon atoms in place of the carboxylic acid and carrying out the reaction in the presence of an effective amount of an hydrolysis catalyst and not less than 1 mole of water per mole of olefin converted.

2. A process as set forth in claim 1, wherein methyl acetate or ethyl acetate is used as the ester.

3. A process as set forth in claim 1, wherein the glycol ester itself is used as the ester.

4. A process as set forth in claim 1, wherein the hydrolysis catalyst is an acid.

5. A process as set forth in claim 1, wherein the oxyacylation is carried out at temperatures of from about 100° to 200° C.

6. A process as set forth in claim 1, wherein the oxyacylation is carried out at pressures of from about 10 to 200 bars.

* * * * *